United States Patent [19]

Jakkula

[11] Patent Number: 4,755,743
[45] Date of Patent: Jul. 5, 1988

[54] METHOD AND APPARATUS FOR MEASURING THE MOISTURE CONTENT OR DRY-MATTER CONTENT OF MATERIALS USING A MICROWAVE DIELECTRIC WAVEGUIDE

[75] Inventor: Pekka Jakkula, Helsinki, Finland

[73] Assignee: Kemira Oy, Helsinki, Finland

[21] Appl. No.: 787,271

[22] Filed: Oct. 14, 1985

[30] Foreign Application Priority Data

Oct. 16, 1984 [FI] Finland ................. 844061

[51] Int. Cl.$^4$ ............................................ G01N 22/04
[52] U.S. Cl. ..................... 324/58.5 B; 324/58.5 A; 324/58.5 R; 343/785
[58] Field of Search ............... 324/58.5 A, 58.5 B, 324/58.5 R, 58 A, 55 B, 58 R, 58.5 C, 58 C; 343/786, 772, 785, 783; 333/208, 209; 73/336.5

[56] References Cited

U.S. PATENT DOCUMENTS

| | | | |
|---|---|---|---|
| 2,794,959 | 6/1957 | Fox | 324/58 B |
| 3,079,551 | 2/1963 | Walker | 324/58.5 R |
| 3,500,182 | 3/1970 | Reed et al. | 324/58.5 R |
| 3,818,333 | 6/1974 | Walker | 324/58.5 A |
| 4,131,845 | 12/1978 | Pakulis | 324/58.5 A |
| 4,201,956 | 5/1980 | Kienberger et al. | 343/783 X |
| 4,203,067 | 5/1980 | Fitzky et al. | 324/58.5 B X |
| 4,206,399 | 6/1980 | Fitzky et al. | 324/58.5 B X |
| 4,600,879 | 7/1986 | Scully et al. | 324/58.5 A |
| 4,651,085 | 3/1987 | Sakurai et al. | 324/58.5 B X |

FOREIGN PATENT DOCUMENTS

| | | | |
|---|---|---|---|
| 0069969 | 1/1983 | Japan | 324/58.5 R |
| 903571 | 8/1962 | United Kingdom | 324/58.5 R |
| 1447896 | 9/1976 | United Kingdom | 324/58.5 A |
| 2057137 | 3/1981 | United Kingdom | 324/58.5 A |

OTHER PUBLICATIONS

Jablonski, Power-Handling Capabilities of Circular Dielectric Waveguide at Millimeter Wavelengths, 2-1985, IEEE, vol. MTT-33, No. 2, pp. 85-89.
Natarajan et al., Microprocessor-Based Microwave Dielectric Measurement of Liquids by Waveguide Plunger Technique, IEEE, IM-34, No. 4, Dec. 1985, pp. 643-646.
Steel, Precision Waveguide Cells for the Measurement of Complex Permittivity of Lossy Liquids and Biological Tissue at 35 GHz, J. Phys. E. Sci. Instrum., 20 (1987), pp. 872-876.
deLoor, Dielectric Properties of Heterogeneous Mixtures Containing Water, The Journal of Microwave Power 3-2, Mar. 1968, pp. 67-73.

Primary Examiner—Reinhard J. Eisenzopf
Assistant Examiner—Jack B. Harvey
Attorney, Agent, or Firm—Biebel, French & Nauman

[57] ABSTRACT

A method and apparatus for measuring the moisture content or dry content of either high or low loss materials having a moisture content in excess of 50% utilizing a dielectric waveguide in contact with the material to be measured. The waveguide may be either embedded into the wall of a process pipe or it may pass through the pipe. The length of the waveguide can be controlled by the addition of reflecting spikes. The waveguide is designed and the microwave frequency so chosen that the microwave signal is reflected at least ten times. The strength of the output microwave signal is a function of the moisture content.

22 Claims, 2 Drawing Sheets

METHOD AND APPARATUS FOR MEASURING THE MOISTURE CONTENT OR DRY-MATTER CONTENT OF MATERIALS USING A MICROWAVE DIELECTRIC WAVEGUIDE

BACKGROUND OF THE INVENTION

1. Field of Invention

The object of the present invention is a method for measuring the moisture content or dry-matter content of a high-loss material or of a low-loss material having a moisture content over 50%. The invention also relates to an apparatus for carrying out the method.

2. Description of the Prior Art

In the process industry, a method is needed for measuirng the moisture content or dry-matter content of materials, a method which operates on a real-time basis, i.e. yields the desired values directly. The values obtained can be used for process control, for example.

Previously, the moisture content of materials has been measured by using conductivity measuring or capacitive measuring, in which the change in the conductivity of a material or in its capacitance is measured as a function of the moisture content. These methods have a disadvantage in their unsuitability for high moisture contents and for materials which contain varying quantities of different ions.

Infrared measuring has also been used, but this method is mainly applicable to solids and gases and not to liquids which form a reflecting mirror surface. Furthermore, infrared meters are sensitive to soiling, as are optical devices in general.

In neutron scatter methods the meters measure the quantity of hydrogen per volume unit. The disadvantage of this method is that it is not applicable to materials which contain varying amounts of other hydrogen-containing substances than water. Another problem is that it requires a large amount of the material to be measured. The method is therefore difficult to apply in a process pipe.

Previously known are also various microwave methods which are based either on the high dielectric constant of water, the so-called reflection or resonance methods, or on its high loss factor, i.e. attenuation methods. One example of the disadvantages of the microwave methods is the unsuitability of the attenuation and resonance methods for measuring the moisture content of high-loss materials. The measuring of high moisture contents is also difficult. The same applies also to the reflection method. The reflection method also involves interference problems in practical measuring structures. An attenuation method can be based either on attenuation measuring or on through-travel attenuation measuring of a surface wave.

SUMMARY OF THE INVENTION

The object of the invention is to provide a method which does not have the above disadvantages. This is accomplished according to the invention by feeding, into a dielectric waveguide which is in contact with the material being measured, a microwave which travels mainly inside the waveguide, and by adjusting the length of the waveguide and the frequency of the microwave in such a way that the microwave is reflected at least once, preferably at least 10 times, from the interface between the material and the waveguide, and by measuring the through-travel attenuation of the waveguide in order to determine the moisture content of the material.

A method in which the length of the waveguide can be adjusted for measuring either low or high moisture contents is especially advantageous. This has proved to be very useful, since the use of waveguides of different lengths makes the method more sensitive either to small or respectively to high moisture contents.

According to the method, it is advantageous to select the dielectric waveguide so that the real component $\epsilon_{r1}$ of its dielectric constant is lower than the real component $\epsilon_{r2}$ of the dielectric constant of the surrounding material being measured.

According to the method according to the invention, the waveguide may be a ring bent to a circular shape, in which case a $TE_{10}$ wave is fed into it, or rod-shaped, in which case a $TE_{10}$ or $TM_{01}$ wave is fed into it.

If the waveguide is rod-shaped, the wave can be fed into one end of the waveguide and received at the other end of the waveguide, or the feeding and the reception may be fitted to the same end.

The apparatus according to the invention is characterized in that is has a waveguide of a dielectric material, the waveguide having means for feeding and receiving a microwave and also means for producing the microwave and means for evaluating the signal received.

The real component $\epsilon_r$ of the dielectric constant of the waveguide is preferably within the range 2–10. The waveguide is thus preferably plastic, rubber, ceramic material, aluminum oxide or tetrafluoroethene. If the $\epsilon_r$ value selected for the waveguide is smaller than the $\epsilon_r$ of the material to be measured, the wave reflecting inside the rod loses energy into the surrounding material in every reflection. The amount of the energy lost in the reflection depends on the proportional difference between $\epsilon_{r1}$ and $\epsilon_{r2}$.

The moisture content of the material being measured is directly proportional to the magnitude of the signal, and inversely proportional to the through-travel attenuation. Preferably the waveguide is circular in shape and located on the inner surface of the pipe which conveys the material to be measured, substantially in a position perpendicular to the travel direction of the material. By embedding the waveguide into the inner surface of the pipe in such a way that the inner surface of the pipe at the waveguide is substantially level, the advantage is gained that the useful life of a waveguide used in conjunction with eroding liquids or slurries lengthens.

The sensitivity of the apparatus improves if the length of the waveguide is adjusted so that several reflections take place. The sensitivity increases as a function of the power of the reflection times. If, for example, the ratio of the signals of two moisture contents is 1.5 with one reflection, it is $1.5^5 = 7.5$ with five, $1.10^{10} = 57$ with ten and $1.5^{20} = 3300$ with twenty reflections.

Reflecting spikes can be fitted in the waveguide, "behind" the feeding means and the receiving means in such a way that a length of free waveguide is left between the said means. These reflecting spikes determine the length of the waveguide and thereby the moisture-content range within which the apparatus is most sensitive. If it is desired to use the same apparatus within different moisture-content ranges, the feeding means may be moved to adjust the length of the waveguide.

If the question is of a circular-shaped rectangular waveguide, it is advantageous that the means feeding in the microwave transmits the wave at such a frequency that a $TE_{10}$ wave is produced in the waveguide.

The waveguide may also be rod-shaped, in which case it runs in the center of the pipe which conveys the material, substantially in a position perpendicular to the longitudinal direction of the pipe. In this case the means for feeding in the microwave are located at one end of the waveguide and the means for receiving the signal at its other end, or both means are at the same end of the waveguide. The means feeding in the microwave is preferably fitted to transmit the microwave at such a frequency and in such a manner that either a $TE_{10}$ or a $TM_{01}$ wave is produced in the waveguide. This is advantageous for the reason that the material being measured affects the rod on each side and the measuring is more sensitive to changes in the moisture content.

BRIEF DESCRIPTION OF THE DRAWINGS

The invention is described below in greater detail with reference to the accompanying figures, in which.

DESCRIPTION OF THE PREFERRED EMBODIMENT

Figure 1:
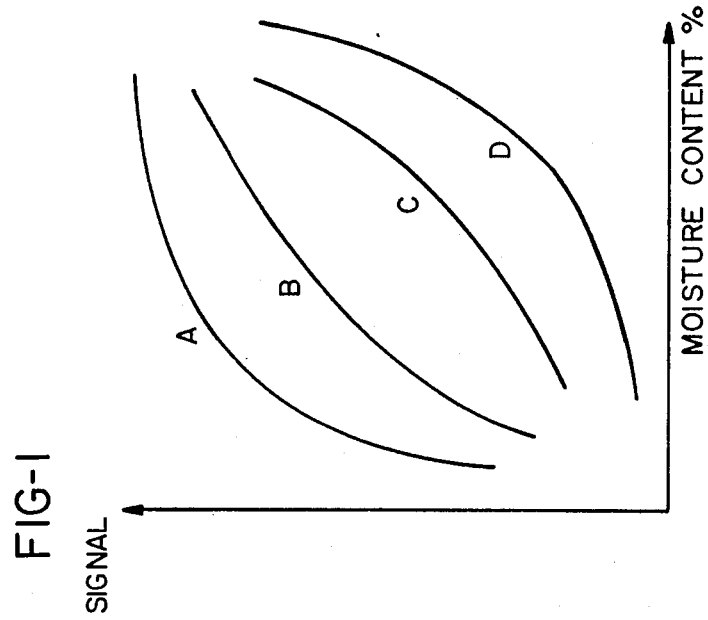
FIG. 1 depicts moisture-content signal curves according to the invention, at different waveguide lengths.

Curve A in FIG. 1 corresponds approximately to a curve obtained by the reflection method. This is accomplished in the waveguide method by adjusting the waveguide to be very short. When the waveguide is lengthened the curve changes, via curves B and C, to curve D, in which the waveguide thus is long. It can be seen from the figure that the arrangement according to curve A is best suited for measuring low and curve D for measuring high moisture contents.

Figure 2:
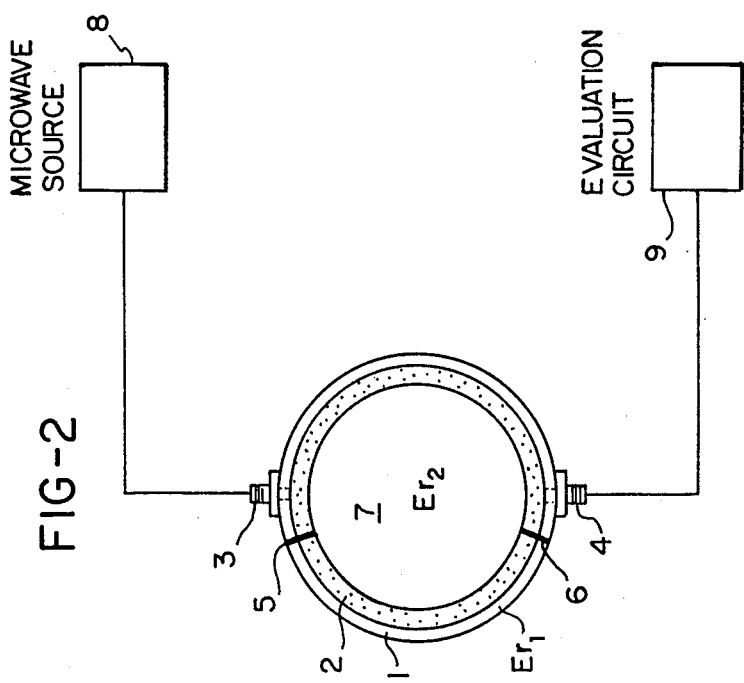
FIG. 2 depicts a sensor structure in which the dielectric waveguide is embedded into the wall of the process pipe.
Figure 3:
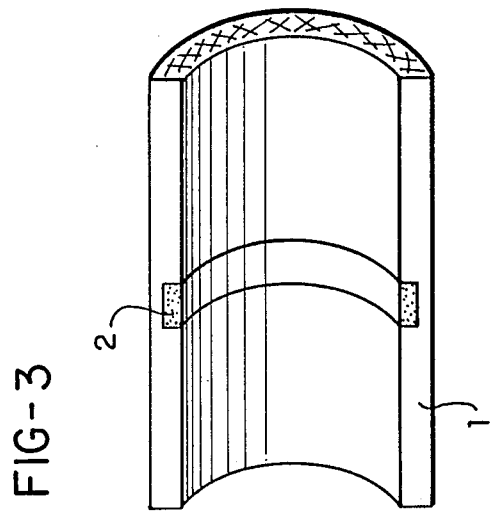
FIG. 3 is a cross sectional perspective representation of the structure according to FIG. 2.

FIGS. 2 and 3 show a process pipe 1 inside which a waveguide 2 has been fitted. The liquid or slurry to be measured travels in space 7 in the pipe. The real component $\epsilon_{r2}$ of the dielectric constant of the material being measured and the real component $\epsilon_{r1}$ of the dielectric constant of the waveguide are also indicated in the figure. Preferably $\epsilon_{r1}$ is smaller than $\epsilon_{r2}$, in which case part of the energy is reflected from the outer surface of the pipe. The figure also shows a microwave power source 8, which via the microwave-feeding connector 3 feeds microwave power into the waveguide. The microwave-receiving connector 4 transmits the received signal further to the evaluation circuit 9, which contains a display unit for indicating the moisture content measured. The figure also shows the reflecting spikes 5 and 6; the length of the waveguide formed between them determines the shape of the curve in FIG. 1. By shifting the location of the feeding means the apparatus can be made sensitive to either low or high moisture contents.

In the arrangement according to the figures, the energy traveling inside the waveguide is thus dependent on the real component $\epsilon_{r2}$ of the dielectric constant of the external medium. Since the dielectric constant of water deviates from the $\epsilon_r$ of most other substances, the moisture content can thus be measured. The higher the moisture content, the greater is the reflection of the microwave from the interface and the lower is the through-travel attenuation and the greater is the signal which is obtained. The measuring can be stabilized by using a reference channel in connection with the evaluation circuit 9. The reference channel can also be realized by allowing the microwave to travel along two routes of different lengths in the dielectric waveguide.

The structure according to FIGS. 2 and 3 has the advantage that the sensor does not form a flow baffle in the process pipe, since the dielectric waveguide is embedded into the wall of the process pipe. Furthermore, the sensor structure is inexpensive and easy to make by turning, and it is well protected, since only the dielectric material used is in direct contact with the liquid being measured. Thus the structure is suitable for contaminated liquids. The structure also measures the mean moisture content over a large area. Furthermore, in the measuring connection there are no interference problems typical of the reflection method.

Figure 4:
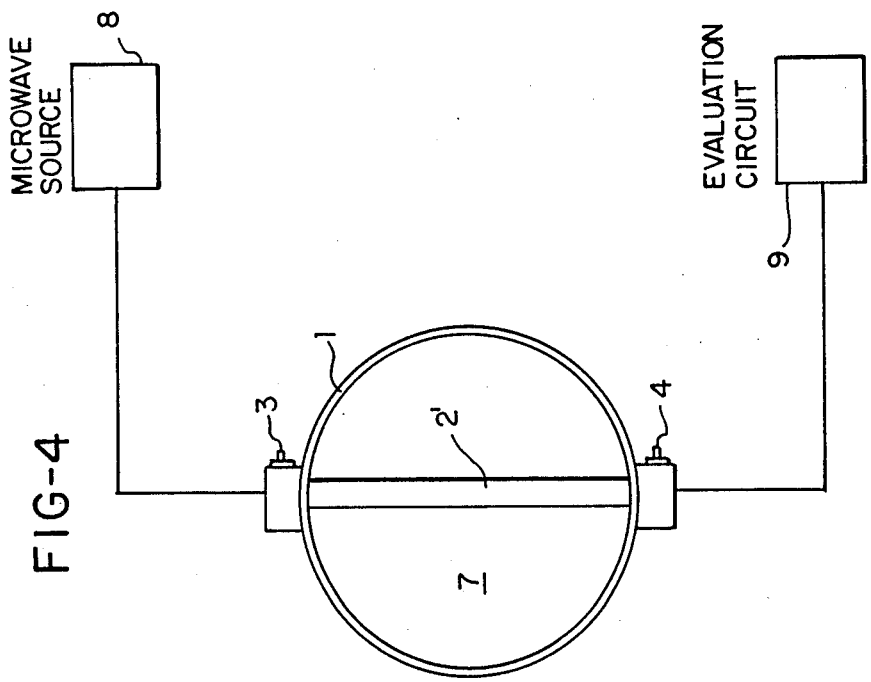
FIG. 4 depicts a sensor structure in which the dielectric waveguide runs through the process pipe.

FIG. 4 shows a corresponding structure in which the dielectric waveguide 2' passes through the process pipe. This structure has the advantage that the material being measured is in contact with the waveguide from all sides, in which case the structure is very sensitive since there are reflections from both sides of the waveguide.

The method and apparatus according to the invention can be used for measuring the moisture content and the dry-matter content of various slurries and liquids. One condition for the liquid to be measured is that its microwave attenuation is great compared with the attenuation of the waveguide, or that its moisture content is high. The contents can also be measured from 2-constitutent solution, in which the real components of the dielectric constants of the constituents of the solution differ from each other.

The method and apparatus are very suitable for measuring the moisture content of fertilizer slurries, methanol, ethanol and acetonitril. Another possible area of application is the measuring of pulp consistency within the range 0–15%, which is a known measuring problem in the wood processing industry.

What is claimed is:

1. A method for measuring the moisture content or dry content of a high or low moss material having a moisture content more than 50%, which comprises the steps of providing of a dielectric waveguide in contact with the material to be measured, feeding a microwave signal into the waveguide at at least one selected input location thereof, the waveguide being so designed and the microwave frequency so chosen, that the microwave travels mainly inside the waveguide and is reflected several, preferably at least ten, times from the interface between the waveguide and the material, and measuring the strength of an output microwave signal at a location of the waveguide spaced apart from said input location, said measured output signal strength indicating the moisture content of the material.

2. A method according to claim 1, characterized in that the length of the waveguide can be adjusted for measuring either low or high moisture contents.

3. A method according to claim 1 or 2, characterized in that the dielectric waveguide is selected in such a way that the real component $\epsilon e_1$ of its dielectric constant is smaller than the real component $\epsilon_{r2}$ of the dielectric constant of the surrounding material to be measured.

4. A method according to claim 1, using a circular waveguide which is fitted on the inner surface of the pipe, around the material to be measured, characterized in that a $TE_{10}$ wave is fed into the waveguide.

5. A method according to claim 1, using a rod-shaped waveguide which is fitted in the middle of the material to be measured, characterized in that either a $TE_{10}$ or $TM_{01}$ wave is fed into the waveguide.

6. A method according to claim 5, characterized in that the wave is fed into one end of the waveguide and received at its outer end.

7. A method according to claim 5, characterized in that the wave is fed in and received at the same end of the waveguide.

8. An apparatus for measuring the moisture content or the dry matter content of a high or low loss material having a moisture content of more than 50%, which comprises
- a dielectric waveguide provided in contact with the material to be measured and having at least one input location and one output location for a microwave signal, said input and output location being spaced apart,
- means for feeding a microwave signal into the waveguide at said input location thereof,
- the waveguide being so designed and the microwave frequency so chosen, that the microwave travels mainly inside the wvaeguide and is reflected several, preferably at least ten, times from the interface between the waveguide and the material,
- means for receiving the output microwave signal at said output location of the waveguide, and
- means for evaluating the received signal so as to obtain an indication of the moisture content of the material.

9. An apparatus according to claim 8, characterized in that the real component $\epsilon r$ of the dielectric constant of the waveguide is 2–10.

10. An apparatus according to claim 9, characterized in that the waveguide is of aluminum oxide.

11. An apparatus according to claim 9, characterized in that the waveguide is of tetrafluoroethene.

12. An apparatus according to claim 8, characterized in that the waveguide is substantially circular-shaped and that it is located on the inner surface of the pipe conveying the material to be measured, in a position substantially perpendicular to the travel direction of the material.

13. An apparatus according to claim 12, characterized in that the waveguide is embedded into the inner surface of the pipe in such a way that the inner surface of the pipe at the waveguide is substantially level.

14. An apparatus according to claim 12, characterized in that the waveguide has at its ends, in connection with the microwave-feeding means and/or receiving means, reflecting spikes between which the wave travels and which have been fitted "behind" the feeding means and/or the receiving means in such a way that free waveguide is left between the said feeding and receiving means.

15. An apparatus according to claim 14, characterized in that there is a third spike fitted in the waveguide in such a way that two waveguides of different lengths are formed, and that there is a microwave transmitter at each end of the waveguide and that the receiver is located at the third spike.

16. An apparatus according to claim 14, charaterized in that the reflecting spikes are screws which have been advantageously screwed in from the outside through the pipe into the waveguide.

17. An apparatus according to claim 14, characterized in that at least one of the feeding points can be shifted in order to adjust the length of the waveguide.

18. An apparatus according to claim 12, characterized in that the means feeding in the microwave transmits the wave at such a frequency that a $TE_{10}$ wave is produced in the waveguide.

19. An apparatus according to claim 8, characterized in that the waveguide is substantially rod-shaped and runs in the center of the pipe conveying the material to be measured, in a position substantially perpendicular to the longitudinal direction of the pipe.

20. An apparatus according to claim 19, characterized in that the means for feeding in the microwave are located at one end of the waveguide and the means for receiving the signal are located at its other end.

21. An apparatus according to claim 19, characterized in that the means for feeding in the microwave and for receiving it are located at the same end of the waveguide, and that the other end of the waveguide is short-circuited.

22. An apparatus according to claim 19, characterized in that the means for feeding in the microwave is fitted to transmit the microwave at such a frequency that either a $TE_{10}$ or a $TM_{01}$ wave is produced in the waveguide.

* * * * *

UNITED STATES PATENT AND TRADEMARK OFFICE
CERTIFICATE OF CORRECTION

PATENT NO. : 4,755,743
DATED : July 5, 1988
INVENTOR(S) : Pekka Jakkula

It is certified that error appears in the above-identified patent and that said Letters Patent is hereby corrected as shown below:

Claim 1, Column 4, line 45, "moss" should be --loss--.

Claim 3, Column 4, line 67, "$\varepsilon e_1$" should be --$\varepsilon r_1$--.

Claim 6, Column 5, line 14, "outer" should be --other--.

Claim 8, Column 5, line 32, "wvaeguide" should be --waveguide--.

Signed and Sealed this

Twenty-ninth Day of November, 1988

*Attest:*

DONALD J. QUIGG

*Attesting Officer*    *Commissioner of Patents and Trademarks*